Figure 1:
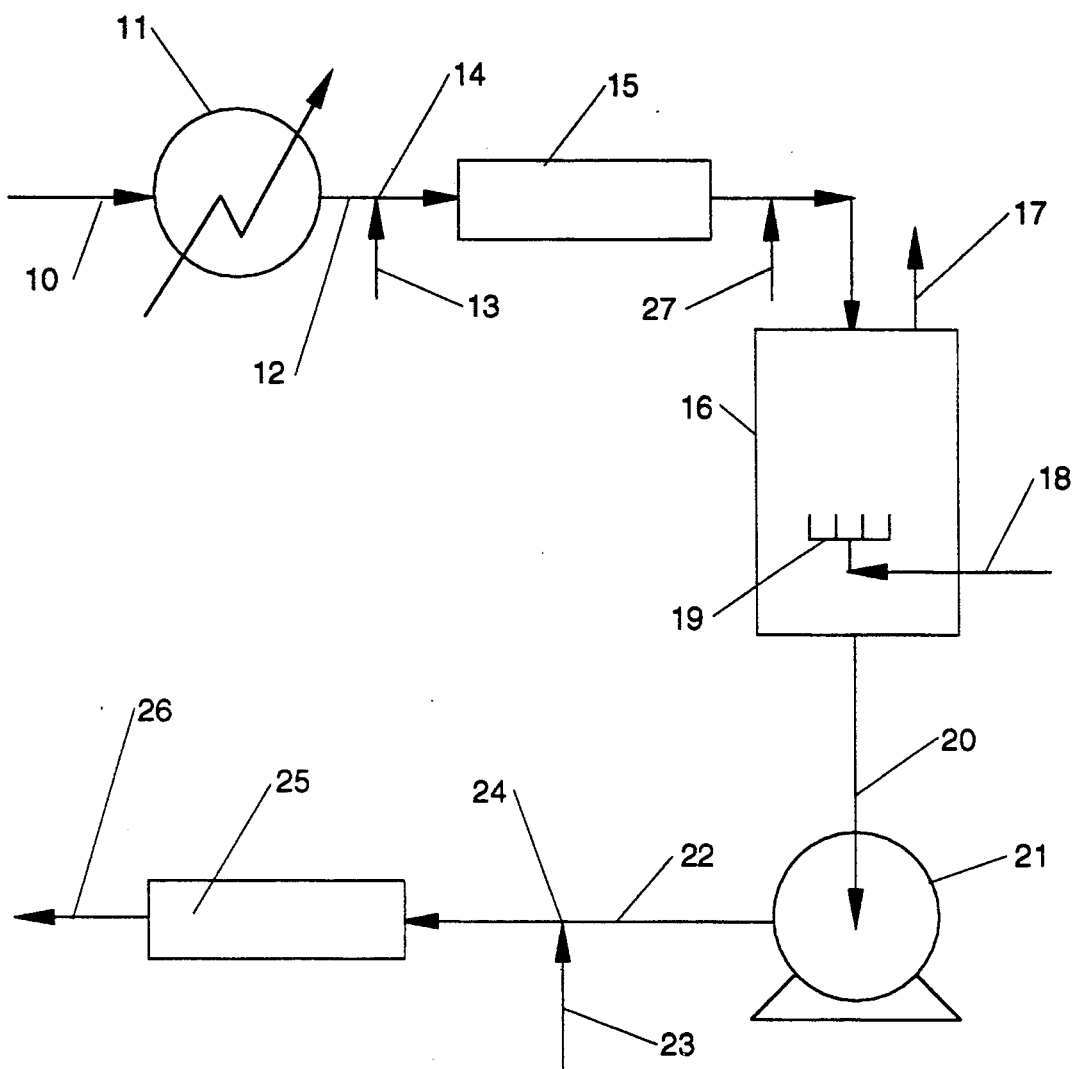

United States Patent [19]

Beharry et al.

[11] Patent Number: 5,315,021
[45] Date of Patent: May 24, 1994

[54] PROCESS FOR REMOVING CHLOROPHYLL COLOR IMPURITIES FROM VEGETABLE OILS

[75] Inventors: Christopher R. Beharry, Cincinnati, Ohio; Levente L. Diosady, Willowdale, Canada; Leon J. Rubin, Toronto, Canada; Ahmed A. Hussein, Toronto, Canada

[73] Assignee: The Procter & Gamble Company, Cincinnati, Ohio

[21] Appl. No.: 907,415

[22] Filed: Jul. 1, 1992

[51] Int. Cl.$^5$ .............................................. C07C 51/42
[52] U.S. Cl. ..................................... 554/190; 554/192
[58] Field of Search ................................. 554/190, 192

[56]  References Cited

U.S. PATENT DOCUMENTS 4,240,972  7/1980  Mag et al. ............................. 554/190
4,280,962  7/1981  Watanabe et al. ................... 554/190

OTHER PUBLICATIONS

Szemraj, H. 1974, Effect of Phosphoric Acid on the Color Change of Rape Seed Oil (in Polish), Tluszeze Jadalne 18, 13.
Szemraj, H. 1973, Review of Technological Methods for Degumming Vegetable Oils (in Polish), Tluszeze Jadalne 17, 4, 169.
Szemraj, H. Phosphoric Acid as a Degumming Agent for Rapeseed Oil (in Polish), Tluszeze Jadalne 17, 5, 213 (1973).
Beagman & Johnson, A New Method for Refining Edible Oils and Fats, Fette Seifew Anstrichmittel v. 66, #3, 1964, pp. 203–206.

Primary Examiner—José G. Dees
Assistant Examiner—Deborah D. Carr
Attorney, Agent, or Firm—Rose Ann Dabek; J. C. Rasser

[57]  ABSTRACT

A process for removing chlorophyll color impurities from vegetable oils, the process comprises:
  i) dispersing a source of phosphoric acid in vegetable oil to form a mixture having a moisture content of less than 0.1% by weight which mixture is maintained at a temperature in the range of 70° C. to 160° C. until a precipitate containing chlorophyll color impurities is formed; and
  ii) at any time thereafter during conventional oil processing up to and including the removal of bleaching clay from the oil, separating the precipitated material from the oil to remove the chlorophyll color impurities with the precipitated material.

12 Claims, 1 Drawing Sheet

PROCESS FOR REMOVING CHLOROPHYLL COLOR IMPURITIES FROM VEGETABLE OILS

FIELD OF THE INVENTION

This invention relates to the treatment of vegetable oils and, more particularly, the removal of chlorophyll color impurities from vegetable oils.

BACKGROUND OF THE INVENTION

Raw vegetable oils obtained from crushing vegetable seeds require considerable processing to provide commercially acceptable products.

The standard processing steps for treatment of vegetable oils are outlined in many reference journals, articles and textbooks. Examples of such treatments are found in "Rape Seed Chemistry and Technology", Elsevier Science Publishers 1990, H. Niewiadomski: "High and Low Erucic Acid Rapeseed Oils", Kramer et al., Academic Press 1983; and Bailey's Industrial Oil and Fat Products, Volume 2, 4th Edition, John Wiley & sons.

The standard steps in the treatment of raw vegetable oils include:

i) degumming of the raw oil to remove by separation hydrophyllic materials which include phospholipids, ii) optionally, phosphoric acid pretreatment of degummed oils may be carried out to remove remaining phospholipids with the removal of at least some chlorophyll color impurities, such precipitate being removed from the treated oils before the next step to avoid the resolubilization of precipitates, iii) neutralizing the oil with a neutralizing agent and separating the developed soaps from the neutralized oil, iv) optionally, water washing the oil to remove the residual soaps developed during neutralization, v) treating the neutralized oil with bleaching clay to remove the remaining chlorophyll color impurities as well as other residual material remaining from neutralization such as soaps, phospholipids and carotenoid compounds, and vi) deodorizing the bleached oil to provide an oil having a commercially acceptable flavor and color.

A process for treating vegetable oils is marketed under the trade-mark ZENITH PROCESS. It is available from Campro Agra Limited, Mississauga, Canada. The ZENITH PROCESS comprises the steps of degumming an oil by use of phosphoric acid, separating the phosphoric acid sludge from the oil, neutralizing the free fatty acids in the oil, removing the developed precipitates including soap stock from the oil and bleaching the oil to remove any remaining chlorophyll color impurities. The process includes a final filtration step and, optionally, a deodorization step. In the ZENITH PROCESS and many other commercially available processes, the degumming step is conducted in the presence of an acid to assist in removal of the non-hydratable forms of phospholipids. It is now fairly common to use citric acid or malic acid as a degumming agent. Phosphoric acid has also been suggested for this purpose. The acid is thought to convert non-hydratable phospholipids to hydratable forms which can then be readily removed from an oil. In the ZENITH PROCESS, such treatment of an oil with phosphoric acid is carried out at temperatures in the range of 35° C. to 50° C. with no control of the moisture content in the oil.

Raw vegetables oils, depending upon their species, contain varying amounts of chlorophyll. It is generally recognized that oil from rapeseed and particular varieties thereof, namely canola, contain very high levels of chlorophyll; frequently, 10 to 30 ppm.

The presence of chlorophyll renders a raw oil a dark black/green color. Such oils also contain high levels of phospholipids commonly called, "gums". Canola and other raw vegetable oils are generally destined for commercial use where a light color is important; therefore, the chlorophyll color impurities have to be removed from the oils before processing into final commercial products.

Raw oil can be processed in accordance with conventional techniques for degumming an oil. Degumming is generally carried out by water treatment in which the hydrophyllic precipitates are removed by centrifugation. Commonly, an acid is used to enhance the removal of non-hydratable forms of phospholipids. Citric acid or malic acid is frequently used in oil degumming processes. When acid is used in deguming a raw oil the degumed oil is commonly referred to as, "superdegummed vegetable oil".

The chlorophyll color impurities are due to the presence of chlorophyll and its derivatives. For purposes of the discussion of this invention, it is understood that wherever the term chlorophyll is used it is intended to also include chlorophyll derivatives and degradation products. These compounds are oxidatively unstable. Their removal enhances the stability of an oil as well as its appearance.

The conventional method to remove chlorophyll color impurities is to use bleaching clay. This clay absorbs the chlorophyll color impurities thereby removing them for the oil. The high chlorophyll content of rapeseed and canola oils requires bleaching clay levels two to three times greater than that needed for other vegetable oils. A method for removing chlorophyll color impurities in canola oil either without the use of bleaching clay or with reduced amounts of clay is desirable so as to reduce both clay costs and oil losses and increase system throughout. Bleaching is often the rate limiting step for processing canola oil.

Investigations concerning the use of phosphoric acid as a degumming agent for vegetable oils and in particular rapeseed oil as well as use of phosphoric acid in the removal of chlorophyll color impurities from rapeseed oil have been reported by Helena Szemraj of the Institute of Fat and Oil Industry, Warsaw, in the papers entitled, "Review of Technological Method for Degumming Vegetable Oils" (1973), "Phosphoric Acid as a Deguming Agent for Rape Seed Oil" (1973) and "Effect of Phosphoric Acid on the Color Change in Rape Seed Oil" (1974). A process is described for reducing chlorophyll color impurities in the oil by treating degummed rapeseed oil having a moisture content not exceeding 0.05% by weight and treating the oils at temperatures in the range of 60° C. to 65° C.. The quantity of phosphoric acid used is in the range of 0.05% through 0.3% by weight of a 75% aqueous solution of phosphoric acid, $H_3PO_4$. In this treatment a precipitate is formed which contains the chlorophyll color impurities. The precipitate is then removed from the oil by filtration using filter paper. This treatment with phosphoric acid reduced the chlorophyll color impurities in the oil. The reduction of the amount of chlorophyll color impurities was determined by spectrophotometric analysis of the oils performed in the visible range of the spectrum at a wavelength of 400 to 750 nm. Additions of 0.05% of 75% $H_3PO_4$ reduced chlorophyll color impurities in the oils by 50% to 70%. Use of 0.1% by weight of 75% H₃PO₄ reduced chlorophyll color impurities in the oil in the range of 60 to 90%. Mixing times in the range of 15 min. were required to effect the necessary precipitation of chlorophyll color impurities from the oil.

The practice described by Szemraj and Bergmann et al., Fette Seifen Anstrichmittel Vol. 66, No. 3, 1964 p. 203-206, "A New Method for Refining Edible Oils and Fats—The Zenith Process", includes removing the precipitate formed by the phosphoric acid treatment before the step of neutralizing the oil because neutralization will re-solubilize the precipitate and cause the chlorophyll color impurities to go back into solution. Hence, a significant drawback of these two techniques is the requirement of an intermediate separation step via filtration or centrifugation prior to neutralization. In a commercial practice, this results in a significant loss of oil plus increased costs of processing.

SUMMARY OF THE INVENTION

A process is provided for removing chlorophyll color impurities from vegetable oils which results in several advantages and features including:

i) the elimination of an additional separation step to remove precipitates containing chlorophyll color impurities from an oil before the oil is neutralized, ii) enhancing the separation of precipitates containing chlorophyll color impurities from oil which has been neutralized, and iii) reducing the amount of bleaching clay required to remove chlorophyll color impurities from treated oil.

According to one aspect of this invention, a process for removing chlorophyll color impurities from vegetable oils during conventional oil processing is provided, the invention comprising:

i) dispersing a source of phosphoric acid in vegetable oil to form a mixture where:
  a) the mixture has a moisture content of less that 0.1% by weight, and
  b) the mixture is maintained at a temperature in the range of 70° C. to 160° C. for a period of time and at a concentration sufficient to develop a precipitate which includes the chlorophyll color impurities, and ii) at any time during conventional processing, up to and including the removal of bleaching clay from the oil, separating the precipitated material from the oil to remove the chlorophyll color impurities with the precipitated material.

In accordance with another aspect of the invention, an improvement is provided in a process for removing chlorophyll color impurities from rapeseed oil or canola oil. The complete process comprises the steps of degumming the oil to remove primarily phospholipid compounds from the oil, treating the degummed oil with a source of phosphoric acid to remove chlorophyll color impurities from the oil in a precipitate, separating the precipitate from the phosphoric acid treated oil prior to neutralizing the oil, neutralizing the oil with a neutralizing agent, separating precipitated material from the neutralized oil and treating the neutralized oil with bleaching clay to remove any remaining chlorophyll color impurities from the oil and, finally, removing the bleaching clay form the oil.

The improvement in the above process comprises treating the degummed rapeseed or canola oil with a source of phosphoric acid before the neutralizing step. Phosphoric acid treatment in accordance with the following conditions eliminates the conventional need for an additional step of separating the precipitate from the oil before the neutralization step. The treatment conditions comprise:

i) dispersing a source of phosphoric acid in rapeseed or canola oil to form a mixture where:
  a) the mixture has a moisture content less than 0.1% by weight;
  b) the mixture is maintained at a temperature in the range of 70° C. to 160° C.; the source of phosphoric acid being at a concentration which develops a precipitate containing chlorophyll color impurities, ii) maintaining the oil at a temperature in the range of 70° C. to 160° C. for a period of time sufficient to allow the precipitate to develop, iii) continuing to process the oil with any formed precipitate resulting from the phosphoric acid treatment until after the neutralization step, iv) removing the precipitate after the neutralization step.

These treatment conditions reduce by at least 50% the amount of bleaching clay ordinarily required to remove the remaining chlorophyll color impurities. Surprisingly and unexpectedly, the soaps which develop during the neutralizing step increase the effectiveness of separating the chlorophyll color impurities from the oil during or after neutralization.

DETAILED DESCRIPTIONS OF THE PREFERRED EMBODIMENTS

Various embodiments of the invention are discussed with respect to reducing the amount of chlorophyll color impurities in the raw or degummed oil to improve the quality of the commercial oil. It is the judicious use of phosphoric acid that is responsible for the surprisingly complete and effective removal of the chlorophyll color impurities. It is surprising that only phosphoric acid works in this invention. Other known degumming acids such as citric acid or malic acid do not work. A range of concentrations of phosphoric acid may be used in the treatment of the oil. Phosphoric acid is intended to include phosphoric acid on a dry basis as well as in an aqueous solution and, in addition, phosphorous pentoxide.

It is also understood that the agents used in neutralizing the treated oil may be various types of basic agents such as sodium or potassium hydroxide or other alkaline agents such as ammonium hydroxide, sodium bicarbonate, sodium carbonate and the like.

The process of this invention is particularly suitable for treatment of canola oil with its high chlorophyll content. The process is also applicable to treating other oils which contain chlorophyll. Such oils include rapeseed oil, soybean oil, sunflowerseed oil, linseed oil, safflowerseed oil and olive oil.

One of the significant advantages of this invention is that the treatment of an oil with phosphoric acid prescribed in the following embodiments eliminates the need for an additional intermediate separation step (via filtration or centrifugation).

The phosphoric acid treatment, for example, may be carried out in conjunction with the degumming of the oils; that is, phosphoric acid may be added to the raw oils before any degumming action takes place. Significantly higher concentrations of phosphoric acid are required in such forms of treatment as will be demonstrated in the following preferred embodiments. At any time prior to the bleaching clay removal step, a phosphoric acid treatment in accordance with this invention provides for a surprising reduction in chlorophyll color impurities in the oil. Consequently, considerably less bleaching clay is required during the final decoloring of the treated oil.

The conditions for the phosphoric acid treatment required to achieve the advantages of this invention are as follows:

i) dispersing a sufficient amount of phosphoric acid in an oil to form a mixture, the mixture having a moisture content of less than 0.1%, and maintaining the mixture at a temperature in the range of 70° C. to 160° C. for a sufficient time to develop a precipitate containing the chlorophyll color impurities;

ii) continuing to process the oil at a temperature above 65° C. until it is opportune to remove the chlorophyll color impurities in the form of a precipitate. This is contrary to conventional processing practices in which a separate filtration or centrificial separation step is used to avoid re-solubilization of the precipitates containing the chlorophyll color impurities. Using the operating conditions of this invention, the precipitate which is formed is stable and can be removed during any of the subsequent processing steps.

Up to 98% of the chlorophyll color impurities in the oil can be removed prior to the final decoloring step. This results in at least about a 50% reduction in the amount of bleaching clay required to remove the remaining color from the oil. This is a significant cost saving because less oil is lost when less clay is used.

Another significant advantage of this invention results from leaving the precipitate in the oil during the neutralization step. In a subsequent separation step, greater and easier separation of the precipitate from the oil is achieved. During the neutralization step, soaps are formed in neutralizing the free fatty acids. These soaps enhance the separation of the precipitate containing the chlorophyll color impurities. Hence, separation of the precipitate by centrifugation, for example, of the neutralized oil is more effective.

The oil to be treated may be processed in various types of equipment suitable for carrying out the phosphoric acid treatment of this invention. Processing can be done in either a batch or continuous fashion.

FIG. 1 is a schematic flow diagram of the equipment which can be used to practice a preferred embodiment of this invention. The feed stock of the system can be either raw oil or degummed oil, super degummed oil, neutralized oil or water washed oil previously processed in a conventional manner.

Concentrations of phosphoric acid in the range of 1% to 5% by weight of the oil on a dry basis are required in treating the raw oil. However, concentrations of phosphoric acid of 1% or less dry weight of $H_3PO_4$ are more than adequate to treat degummed oils. With 75% to 85% solutions of phosphoric acid, approximately 0.05% to 1.0% by weight on a dry basis of $H_3PO_4$ is required for treating degummed, neutralized or water washed oils.

In FIG. 1, a vegetable oil is removed from an upstream storage tank and enters the system through line 10. The incoming oil is heated to the desired reaction temperature of 70° C. to 160° C. in heat exchange 11 before phosphoric acid is mixed with the oil in mixer 15 which may be a static vane mixer. The phosphoric acid is introduced to line 12 through line 13 at junction 14. After the phosphoric acid is mixed with the oil, the oil and acid mixture enters reaction vessel 16 which is under a vacuum drawn through line 17. To provide for better mixing within the vessel 16 and for improved drying, nitrogen can be introduced through line 18 to distributor 19. Upwardly flowing nitrogen bubbles cause a gentle mixing of the oil and acid mixture within the vessel and also provides sufficient stripping action to drive off excess moisture. Since the preferred treatment system is continuous, the residence time for the oil and acid mixture in vessel 16 is sufficient to allow the precipitation of the chlorophyll color impurities from the oil. A suitable steady state flow rate into and out of the vessel is chosen to achieve the required reaction time. The properly treated oil is removed through line 20 by pump 21.

Depending upon the type of oil feed stock selected, the process continues in one of the following manners:

a) For raw oils, degumming is the next step. The acid treated oil is passed through line 22 to mixer 25 which may be a static vane mixer. The degumming step is effected by introducing water (preferably softened water having less than 20 grains hardness) through line 23 into line 22 at junction 24. After mixing of the water in the oil, the mixture is transferred to a stirred residence time vessel prior to separation via centrifugation. Thereafter, other treatment procedures can be applied to the oil in accordance with conventional techniques which include neutralization, bleaching, hydrogenation, deodorization.

b) For water degummed or superdegummed oils, neutralization is generally the next step. The neutralization step can be carried out by introducing a basic solution (preferably sodium hydroxide) through line 3 into line 22 at junction 24. After mixing of the basic solution into the oil, the neutralized oil is transferred to a stirred residence time vessel prior to separation via centrifugation. Thereafter, other treatment procedures can be applied to the oil in accordance with conventional techniques which include water washing, bleaching, hydrogenation and deodorization.

c) For a neutralized oil that has not yet been washed, the acid treated oil is passed through line 22 to mixer 25. The water washing is effected by introducing softened water, preferably water of less than 20 grains hardness, through line 23 into line 22 at junction 24. After mixing of the water in the oil, the mixture is separated. Other treatment procedures can thereafter be applied to the oil in accordance with conventional techniques which include bleaching, hydrogenation and deodorization.

d) For water washed oil where the next step is bleaching, the acid treated oil is passed through line 22 and into mixer 25. Bleaching is initiated by introducing a bleaching clay slurry through line 23 into line 22 at junction 24. After mixing, the bleaching clay and oil mixture is sent to a bleaching vessel which provides the residence time needed to effect the bleaching action. Thereafter, the clay is separated from the oil by filtration. Alternately, the bleaching clay may be added directly to vessel 16 by feeding a bleaching clay slurry to line 14 through line 27. The acid treatment and bleaching steps are carried out simultaneously without losing any of the advantages of this invention. Additional agitation may be required in vessel 16 to maintain the bleaching clay in suspension. After leaving vessel 16, the oil/acid/clay mixture is sent directly to a filtration system. After the filtration step, other standard treatment procedures may be applied to the oil which include hydrogenation and deodorization.

In the treatment of vegetable oils in general and canola oil in particular, the reaction vessel 16 is typically maintained at a temperature in the range of 80° C. to 105° C.. The vacuum applied to the tank is sufficient to remove excess moisture and is generally under 10 mmhg. The vacuum assures the moisture content of the oil in the reaction vessel is below 0.1% by weight, preferably below 0.07% by weight and, more preferably, less than 0.04% by weight. The residence time in the vessel should be between 1 and 60 minutes at the temperatures specified and preferably between 10 and 30 minutes. Residence time and temperature are generally related; the higher the temperature in the reaction vessel the shorter the residence time required to process the oil.

Various embodiments of the invention have been investigated. The results of these investigations are reported in the following tables.

Tables 1 and 2 show the effect of phosphoric acid reaction temperature and reaction time on the development of a stable chlorophyll precipitate. Degummed canola oils were used as the feed stock.

Table 1 shows the effect that reaction temperature has on developing a stable precipitate containing chlorophyll color impurities before and after neutralization for reaction times of 1 minute. Data collected prior to neutralization were collected by adding a filter aid to the samples taken and centrifuging to remove the precipitate. The filter aid acted as an agent to capture the precipitate.

TABLE 1

EFFECT OF TEMPERATURE ON CHLOROPHYLL REDUCTION

| STOCK TYPE | PHOSPHORIC ACID LEVEL* (%) | ACID REACTIONS CONDITIONS | | CHLOROPHYLL LEVELS | |
|---|---|---|---|---|---|
| | | TIME (MIN) | TEMP (°C.) | POST ACID (ppm) | POST NEUTRALIZATION (ppm) |
| DE-GUMMED CANOLA | NONE | — | — | — | 13.2 |
| DE-GUMMED CANOLA | 0.33 | 1 | 82 | 1.2 | 3.5 |
| DE-GUMMED CANOLA | 0.33 | 1 | 96 | 0.9 | 1.5 |
| DE-GUMMED CANOLA | 0.33 | 1 | 102 | 0.9 | 1.3 |
| DE-GUMMED CANOLA | 0.33 | 1 | 104 | — | 0.8 |

*on a dry basis

As set out in Table 1, reaction temperature within the range used, has only a slight effect on precipitate removal prior to neutralization, i.e., all temperatures demonstrated good removal efficiencies. However, after neutralization, reaction temperature had a significant effect on stability of the precipitate. At the lower reaction temperatures a significant amount of the precipitate went back into solution and was not removed during neutralization. For one minute reaction time the tendency for the precipitate to resolubilize was essentially eliminated at about 100° C.

TABLE 2

EFFECT OF HOLD TIME ON CHLOROPHYLL REDUCTION TO 1 PPM

| STOCK TYPE | ACID REACTION CONDITIONS | |
|---|---|---|
| | TEMP (°C.) | TIME (MIN.) |
| DEGUMMED CANOLA | 54 | 100 |
| DEGUMMED CANOLA | 82 | 10 |
| DEGUMMED CANOLA | 104 | 1 |

Table 2 shows the relationship between the reaction time required to reach chlorophyll levels less than 1 ppm after neutralization for various acid reaction temperatures. As set out in Table 2, the temperature effect shown previously at 1 minute reaction time can be overcome if enough additional reaction time is provided. In a continuous flow refining system, reaction times shorter than 30 minutes and more appropriately shorter than 15 minutes are desired so that the time the system takes to respond to changes can be easily managed. Acid reaction temperatures greater than 70° C. and more appropriately above 80° C. meet this criteria for continuous refining.

Acid treatment temperatures in excess of 120° C. may effect the finished deodorized oil color by producing a darker yellow colored oil as shown in Table 3. Therefore, temperatures below 120° C. are preferred.

TABLE 3

ACID REACTION TEMPERATURE EFFECT ON DEODORIZED COLORS

| ACID REACTION TEMPERATURE (°C.)* | DEODORIZED** YELLOW COLOR (LOVIBOND SCALE) |
|---|---|
| 49 | 1.1 |
| 71 | 1.1 |
| 96 | 1.4 |
| 126 | 2.1 |
| 177 | 3.9 |

*Acid Treatment Condition: 30 minutes reaction time, 0.38% $H_3PO_4$ dry weight. Samples were lye refined and then bleached with 1% acid activated clay (Filtrol 105).
**Samples were batched deodorized at 263° C. for 2 hours.

Moisture content of the acid treated oil has a significant effect on the removal of chlorophyll color impurities. The moisture content of the mixture should be less than 0.1% by weight. Table 4 shows that removal of chlorophyll color impurities improves steadily with decreasing moisture content. The preferred moisture content is l e s s then 0.07% by weight. The reaction conditions are in accordance with the procedure followed in developing the results given in Tables 1 and 2. The reaction time was about 1.0 minutes. Vacuum was applied to the heated mixture to reduce moisture levels to the extent indicated. The acid treated samples were mixed with a filter aid and then centrifuged to remove the precipitate containing the chlorophyll color impurities.

TABLE 4

EFFECT OF MOISTURE LEVEL

| MOISTURE LEVEL (% by weight) | ACID REACTION TEMPERATURE (°C.) | POST ACID CHLOROPHYLL LEVEL (ppm) |
|---|---|---|
| 0.13 | 104 (No Vacuum) | 10.7 |
| 0.09 | 72 (Vacuum) | 8.2 |
| 0.07 | 73 (Vacuum) | 2.3 |
| 0.04 | 82 (Vacuum) | 1.1 |

TABLE 4-continued

| EFFECT OF MOISTURE LEVEL | | |
|---|---|---|
| MOISTURE LEVEL (% by weight) | ACID REACTION TEMPERATURE (°C.) | POST ACID CHLOROPHYLL LEVEL (ppm) |
| 0.03 | 102 (Vacuum) | 0.9 |
| 0.02 | 96 (Vacuum) | 0.9 |
| 0.01 | 105 (Vacuum) | 0.7 |

Table 5 sets out the amount of phosphoric acid required to achieve the desired level of chlorophyll removal. The amount of phosphoric acid used is reported on a dry weight basis. The oil/acid mixture moisture content was less than 0.04% by weight in all instances. The reaction temperatures and times are as indicated in Table 5. For purposes of testing removal of chlorophyll color impurities, data were collected after acid treatment but prior to neutralization. As before, the acid treated samples were taken and mixed with filter aid and centrifuged to aid in removal of precipitate containing chlorophyll color impurities.

TABLE 5

| EFFECT OF STOCK TYPE ON REQUIRED PHOSPHORIC ACID LEVEL AT 71° C. | | | | |
|---|---|---|---|---|
| STOCK TYPE | DRY ACID LEVEL (%) | ACID REACTION CONDITIONS TIME (MIN) | TEMP (°C.) | POST ACID CHLOROPHYLL LEVEL (ppm) |
| DEGUMMED CANOLA | 0.19 | 15 | 71 | 5.3 |
| DEGUMMED CANOLA | 0.26 | 15 | 71 | 2.0 |
| DEGUMMED CANOLA | 0.38 | 15 | 71 | 0.4 |
| DEGUMMED CANOLA | 0.56 | 15 | 71 | 0.3 |
| RAW CANOLA | 0 | 30 | 121 | 16 |
| RAW CANOLA | 0.38 | 30 | 121 | 9.9 |
| RAW CANOLA | 1.5 | 30 | 121 | 3.1 |
| RAW CANOLA | 3 | 30 | 121 | 0.7 |
| RAW CANOLA | 4.5 | 30 | 121 | 0 |

Table 5 shows that there is a steady decline in the amount of chlorophyll color impurities remaining in an oil after the separation step as the concentration of phosphoric acid is increased.

In the particular lot of degummed canola oil used in the series of tests reported in Table 5 there is very little difference in the amount of chlorophyll color impurities removed from the oil when the concentration of acid is higher than 0.26% phosphoric acid on a dry basis. This level of acid treatment (i.e. 0.26%) has been found to work well in a continuous commercial process in which degummed canola oil is the starting material. Hence, the preferred concentration of phosphoric acid for treating degummed canola oil is about 0.25% by weight on a dry basis. Depending upon the type of oil and its source, the amount of phosphoric acid required to remove chlorophyll color impurities to an acceptable level will vary considerably. Based on further experience with degummed canola oil, the preferred range for the concentration of phosphoric acid is used from 0.05% to 1% by weight on a dry weight basis.

For the particular lot of raw canola oil used in this series of tests, there was very little improvement in the amount of chlorophyll color impurities removed past about 2% by weight of phosphoric acid on a dry basis. Hence, the preferred concentration of phosphoric acid for treating raw canola oil is in the range of 2% by weight on a dry basis. It is appreciated, however, that depending upon the type of raw oil and its source, the amount of phosphoric acid required to remove chlorophyll color impurities to an acceptable level may vary considerably. The desired range of phosphoric acid used to process a raw oil is from 0.5% to 5% by weight on a dry weight basis.

Table 6 summarizes the effect of refining temperature on refined oil quality. Degummed canola oil was acid treated at 104° C. with 0.38% on a dry basis of phosphoric acid and held for 15 minutes to allow the precipitate to fully develop. The oil was neutralized and centrifuged to remove precipitate at the noted refining temperature. The oil was subsequently water washed and recentrifuged. The amount of the chlorophyll impurities remaining in the oil was determined after the second time the oil was centrifuged.

TABLE 6

| EFFECT OF REFINING TEMPERATURE ON CHLOROPHYLL REDUCTION | | |
|---|---|---|
| REFINING TEMPERATURE (°C.) | RWW* CHLOROPHYLL (ppm) | COMMENTS |
| 38 | 1.6 | Unbreakable Emulsion |
| 54 | 1.4 | Unbreakable Emulsion |
| 66 | <0.3 | Normal Emulsion |
| 82 | <0.3 | Normal Emulsion |

*RWW = Refined Water Washed

Neutralizing and centrifuging at temperatures above 66° C. provides for optimum chlorophyll color impurity removal. While temperatures lower than this provide reasonable reduction in chlorophyll color impurities, the formation of "unbreakable" emulsions causes increased losses during centrifugation and/or forces the processing system to be run at a lower than desired rate to obtain adequate separation of the neutralized oil from the aqueous phase.

To demonstrate the application of this invention in conjunction with a bleaching operation, test were performed on refined water washed canola oil that had not previously been treated in accordance with this invention. Samples of this oil were batch bleached at 121° C. for 30 mixtures using a vacuum bleaching vessel. The data collected are reported in Table 7.

TABLE 7

| CHLOROPHYLL REDUCTION DURING BLEACHING Feed Stock = Refined Water Washed Canola Oil Chlorophyll Content = 6.7 ppm | | | |
|---|---|---|---|
| Run | Percent Acid (%) | Percent Clay (%) | Finished Chlorophyll Level (ppm) |
| Control | None | 2.4 | 0.01 |
| Test 1 | 0.19 | 0.8 | 0.04 |
| Test 2 | 0.23 | 0.8 | 0.01 |

The control sample, which was not processed in accordance with this invention, required 2.4% bleaching clay to reduce the chlorophyll content from 6.7 ppm to the commercially acceptable level of 0.01 ppm. In the test runs, phosphoric acid was added on a dry weight basis as indicated along with the bleaching clay and processed in accordance with this invention. After filtering the clay from the oil, the level of chlorophyll was the same (or nearly the same) as in the control. This was achieved using 67% less bleaching clay.

It is appreciated that a variety of bleaching clays can be used in this embodiment such as those sold under the trade-marks FILTROL-105, ACTISYL and CLARION 470.

To further demonstrate that this invention is applicable to many oils, other studies were performed on samples of degummed soybean oil and degummed sunflowerseed oil. The degumming was carried out by mixing the raw oils with 4% soft water at room temperature for 10 minutes and centrifuged to split the phases. In accordance with this invention samples of these degummed oils were treated with 0.3% phosphoric acid on dry weight basis, heated/dried under vacuum to 82° C. and mixed for 15 minutes. The samples were then neutralized with excess sodium hydroxide, separated by centrifugation, water washed and dried. The data collected is given in Table 8.

TABLE 8

OTHER OILS

| Run | Oil | Treated | Chlorophyll Levels (ppm) Degummed | Chlorophyll Levels (ppm) Post Acid | Chlorophyll Level (ppm) Post Refining |
|---|---|---|---|---|---|
| Control | Soybean | NO | 0.7 | — | 0.6 |
| Test | Soybean | YES | 0.7 | 0 | 0 |
| Control | Sunflower | NO | 0.5 | — | 0.3 |
| Test | Sunflower | YES | 0.5 | 0 | 0 |

As can be determined from Table 8, chlorophyll color impurity removal is superior when an oil is processed in accordance with this invention compared to conventionally treated oils. In this particular example, the chlorophyll level in the soybean and sunflower test samples was reduced to zero after a refining step. After refining the level of chlorophyll in the two control was unacceptably high.

As a part of the phosphoric acid treatment, sufficient excess neutralizing agent must be used to neutralize the free fatty acids naturally present in the oil and any phosphoric acid that remains in the oil. The amount of neutralizing agent required to neutralized the free fatty acids is readily determined and is well understood by those skilled in the art. The "excess" is the amount of neutralizing agent used to drive reaction to completion. This excess is typically 3-20% by weight for most oils which have not been treated with acid. Phosphoric acid treated oils will require a still greater excess of neutralizing agent. This increase in the amount of neutralizing agent adds slightly to the overall processing costs. It is well offset by the decreased usage of bleaching clay, reduced loss of oil and the avoidance of an additional separation step.

Although preferred embodiments of the invention have been described in detail, it will be understood by those skilled in the art that variations may be made without departing from the spirit of the invention or the scope of the appended claims.

We claim:

1. A process for removing up to 98% of the chlorophyll color impurities from vegetable oils comprising:
    (a) dispersing a source of phosphoric acid in a vegetable oil to which has a moisture content of less the 0.1% by weight at a temperature of 70° C. to 160° C. and at a pressure of less than 10 mm of mercury, for a time sufficient to develop a precipitate of said chlorophyll color impurities; and
    (b) subjecting the vegetable oil containing the chlorophyll color precipitates to further processing steps selected from the group consisting of degumming, water washing, neutralization, or bleaching; and
    (c) removing the precipitated chlorophyll color impurities during the subsequent processing.

2. A process of claim 1 wherein said vegetable oil is selected from the group consisting of rapeseed oil, soybean oil, sunflowerseed oil, linseed oil, safflowerseed oil and olive oil.

3. A process of claim 2 wherein the variety of rapeseed oil is canola oil.

4. A process of claim 1 wherein said source of phosphoric acid is selected from the group consisting of phosphoric acid, phosphorus pentoxide or aqueous solutions of phosphoric acid containing 75% to 85% by weight of $H_3PO_4$.

5. A process of claim 4 wherein the concentration of $H_3PO_4$ dispersed in said oil is in the range of 0.05% to 5.0% by weight on a dry basis for $H_3PO_4$.

6. A process according to claim 1 comprising neutralizing said phosphoric acid treated oil which includes said precipitate with a neutralizing agent selected from the group consisting of aqueous solutions of sodium or potassium hydroxide or other alkaline agents selected from the group consisting of ammonium hydroxide, sodium bicarbonate and sodium carbonate in step b).

7. A process of claim 6 wherein said neutralizing step is conducted at a temperature in the range of 65° C. to 105° C..

8. A process of claim 1 wherein said phosphoric acid treatment step is conducted at a temperature in the range of 80° C. to 105° C..

9. In a process for removing up to 98% of the chlorophyll color impurities from a vegetable oil, said process comprising the steps of optionally degumming said oil to remove primarily hydratable phospholipid compounds from said oil, treating said oil with a source of phosphoric acid to remove chlorophyll color impurities from said oil in the form of a precipitate, separating said precipitate from said oil prior to neutralizing said oil, separating precipitated material from said neutralized oil and treating said neutralized oil with bleaching clay to remove remaining chlorophyll color impurities from the oil and removing said bleaching clay from the oil, the improvement which comprises treating said vegetable oil with a source of phosphoric acid in accordance with the following conditions which eliminate the need to separate said precipitate from said oil before said neutralization step, said treatment conditions comprising:
    i) dispersing said source of phosphoric acid in said oil to provide a mixture of acid and oil which is maintained at a temperature in the range of 70° C. to 160° C. and has a moisture content of less than 0.1% by weight, said source of phosphoric acid being sufficient to develop a precipitate containing chlorophyll color impurities, ii) maintaining said oil at said temperature for a period of time sufficient to allow said precipitate to develop,
iii) continuing to process said oil with said precipitate until after said neutralization step,
iv) removing the precipitate from said oil after said neutralizing step, such treatment being sufficient to reduce the amount of bleaching clay required to remove any chlorophyll color impurities remaining in said oil after neutralizing said oil.

10. The process of claim 9 wherein said vegetable oil is selected from the group consisting of rapeseed oil, soybean oil, sunflowerseed oil, linseed oil, safflowerseed oil and olive oil.

11. The process of claim 10 wherein the variety of rapeseed oil is canola oil.

12. The process of claim 11 wherein the concentration of $H_3PO_4$ dispersed in said oil is in the range of 0.05% to 1.0% by weight on a dry basis for $H_3PO_4$.

* * * * *